United States Patent
Cummins et al.

(10) Patent No.: US 9,335,297 B1
(45) Date of Patent: May 10, 2016

(54) FLOW SENSING DEVICE

(71) Applicant: WaterTally, Inc., Santa Ana, CA (US)

(72) Inventors: Ryan M. Cummins, Santa Ana, CA (US); Thomas M. Cummins, Santa Ana, CA (US)

(73) Assignee: WaterTally, Inc., Santa Ana, CA (US)

( * ) Notice: Subject to any disclaimer, the term of this patent is extended or adjusted under 35 U.S.C. 154(b) by 647 days.

(21) Appl. No.: 13/774,530

(22) Filed: Feb. 22, 2013

Related U.S. Application Data

(60) Provisional application No. 61/602,785, filed on Feb. 24, 2012.

(51) Int. Cl.
  *G01F 1/66* (2006.01)
  *G06F 19/00* (2011.01)
  *G01N 29/036* (2006.01)

(52) U.S. Cl.
  CPC .............. *G01N 29/036* (2013.01); *G01F 1/66* (2013.01)

(58) Field of Classification Search
  CPC ........... G01F 1/66; G01F 1/666; G01F 1/684; G01M 3/24; G01N 29/036
  USPC ........... 702/45, 47, 48, 50, 51, 54, 66, 71, 75; 73/861; 137/389, 468; 239/71; 340/573.1, 606; 700/282
  See application file for complete search history.

(56) References Cited

U.S. PATENT DOCUMENTS

| | | | |
|---|---|---|---|
| 6,323,774 B1 | 11/2001 | Mitchell | |
| 7,742,883 B2 | 6/2010 | Dayton et al. | |
| 7,857,234 B2 | 12/2010 | Daley et al. | |
| 2008/0110279 A1 | 5/2008 | Grueber | |
| 2009/0106891 A1 | 4/2009 | Klicpera | |
| 2010/0145479 A1 | 6/2010 | Griffiths | |
| 2010/0263742 A1 | 10/2010 | Bogdanska | |
| 2011/0031331 A1 | 2/2011 | Klicpera | |
| 2011/0068192 A1 | 3/2011 | Klicpera | |
| 2011/0068931 A1 | 3/2011 | Abernethy et al. | |
| 2011/0114202 A1 | 5/2011 | Goseco | |
| 2011/0166714 A1 | 7/2011 | Stachnik | |
| 2011/0178644 A1 | 7/2011 | Picton | |
| 2011/0186154 A1 | 8/2011 | Klicpera | |
| 2011/0260827 A1 | 10/2011 | Shapiro et al. | |
| 2011/0265890 A1 | 11/2011 | Killian | |
| 2013/0085688 A1* | 4/2013 | Miller | G01F 1/66 702/48 |

OTHER PUBLICATIONS

Gaddam, A., "Smart home for elderly care using optimized number of wireless sensors", IEEE Xplore Digital Library,.Dec. 14-16, 2009; Sch. of Eng. & Adv. Technol., Massey Univ. (Turitea), NZ, 1 page.

* cited by examiner

*Primary Examiner* — John H Le
(74) *Attorney, Agent, or Firm* — Knobbe, Martens, Olson & Bear LLP

(57) ABSTRACT

A non-invasive, hands-free "water flow device" senses when water is and is not flowing and can give the user a visual display, of the real time water flow duration and quantity of water used by a shower (or other water dispensing device), for example. The water flow device may use an acoustic transducer (e.g., a microphone) to sense the acoustic waves generated by the flow of water during a shower. For example, the flow or lack of flow of water may be determined by analyzing the acoustic signature and/or amplitude of sounds (e.g., within a certain frequency range) in the shower.

22 Claims, 7 Drawing Sheets

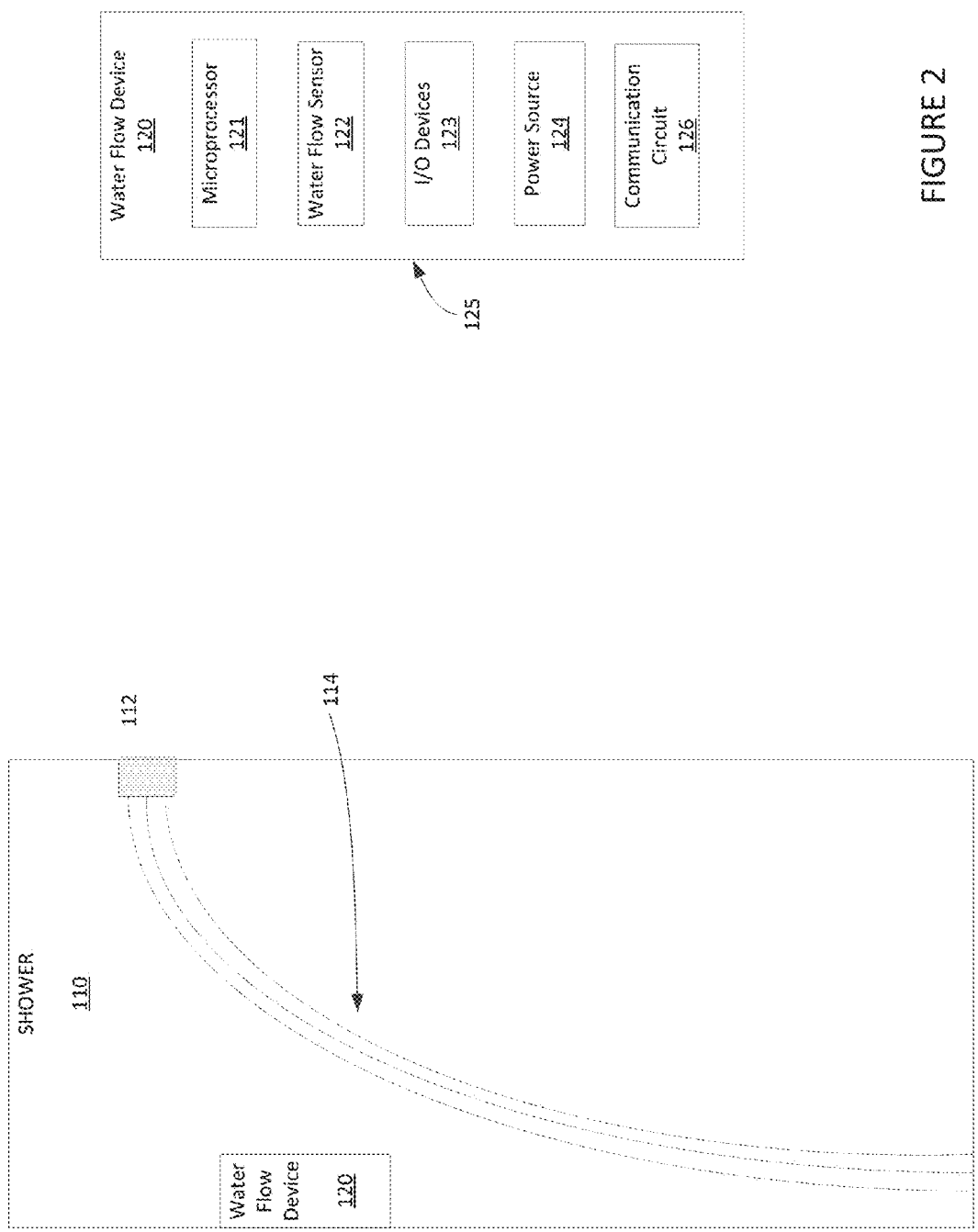

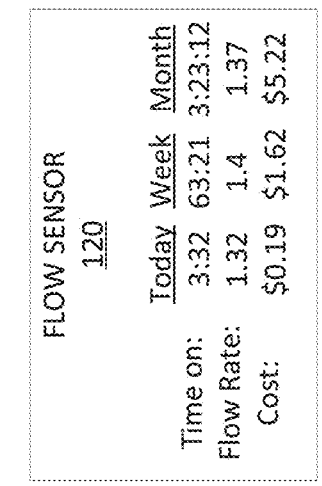
FIGURE 2C
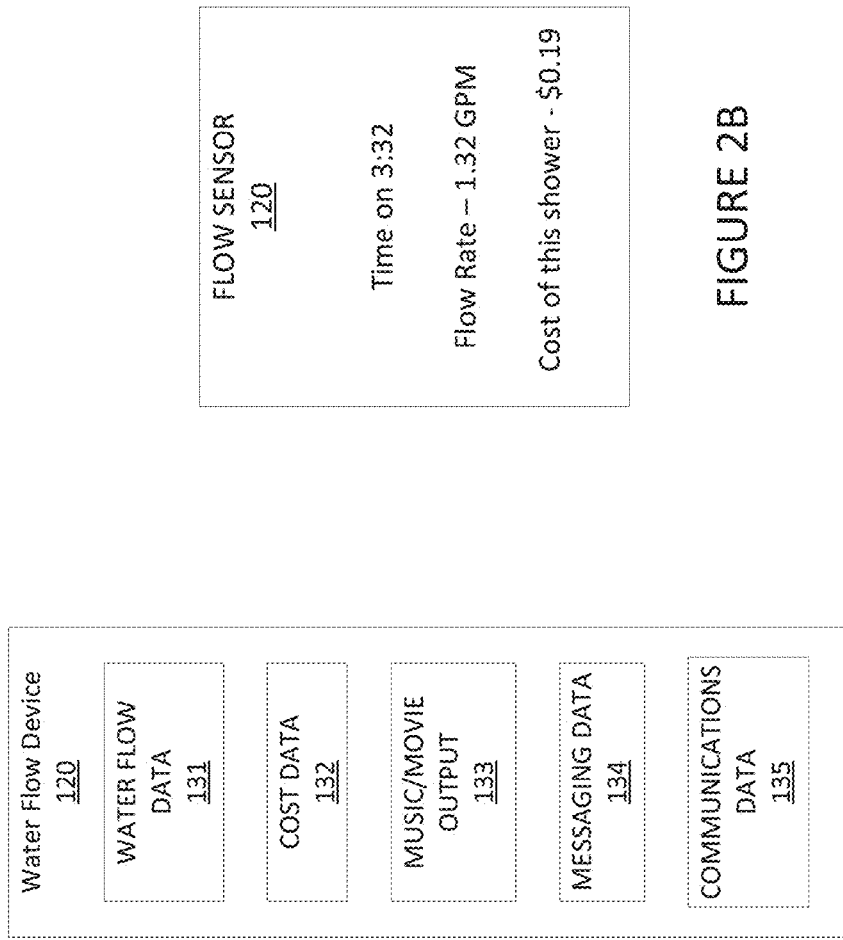
FIGURE 2B
FIGURE 2A

FLOW SENSING DEVICE

CROSS-REFERENCE TO RELATED APPLICATIONS

This application claims the benefit of U.S. Provisional Application No. 61/602,785, filed on Feb. 24, 2012, the entirety of which is hereby incorporated herein by reference.

BACKGROUND

People are often unaware of the amount of resources they consume on a daily basis, water being one of the most precious of these resources. The volume of water consumed by a single individual in one day can be staggering, and with growing global environmental concerns, practices of sustainable behavior will become increasingly important in the future. For many daily activities, no thought is given to the amount of water wasted in processes like washing hands, washing dishes or even taking a shower.

Many activities such as showering are essential to maintain a normal and healthy lifestyle. However, some activities such as showering present very real challenges and dangers for those with disabilities or health concerns, most notably seniors. Every year thousands of elderly men and women suffer serious injury or even death from bathroom related incidents, such as falling.

SUMMARY

Described herein are various embodiments of non-invasive, hands-free "water flow devices" that can sense when water is and is not flowing and can give the user a visual display, of the real time water flow duration and quantity of water used by a shower (or other water dispensing device). In some embodiments, the water flow device can be non-visual (e.g., without a display) and monitor the real time water flow duration. In one embodiment, the water flow device employs an acoustic transducer (e.g., a microphone) to sense the acoustic waves generated by the flow of water during a shower. For example, the flow or lack of flow of water may be determined by analyzing the acoustic signature of sounds in the shower. The water flow device may be designed to process raw signals from an acoustic sensor in order to sense for only the acoustic signal generated by water flowing, such as in a pipe or as it exits a faucet or shower head. Advantageously, the water flow devices discussed herein automatically sense when the water flow begins and ends and are non-invasive, hands-free, and automated. In other embodiments, a water flow device may be configured to detect water flow in another component, such as hose, sprinkler or faucet.

In one embodiment, the water flow devices discussed herein are easy to install, such that they may be installed without any plumbing, electrical, or other technical knowledge. Instead, the user (e.g., an ordinary consumer) may simply place the device anywhere in the shower, or other area near a piped water source, and the water flow device is ready to begin sensing water flow. More particularly, the water flow devices discussed herein may not require integration into existing plumbing or hardware. Accordingly, the water flow devices can be installed by ordinary consumers, without the need to pay a professional to install the device, and can easily adapt to all different types of plumbing, shower hardware, faucets, sinks, bathtubs, industrial water supply pipes, sprinklers, irrigation pipes or any other water delivery means where water flow measurement is needed. Thus, discussion herein of monitoring flow of water in a shower should be interpreted to cover measurement of water (or other fluid) in any other environment and/or from any other delivery mechanism.

In other embodiments, the water flow devices could be configured so that they can measure other fluids such as gases or liquids (e.g. Atmospheric air, purified air, pure oxygen, helium, hydrogen, etc. or water based liquids, alcohol based liquids, etc.) in various fluid delivery mechanisms (e.g. pipes, valves, etc.) or that is airborne, in the same or similar manners as discussed herein with reference to water. Thus, references to "water" should be also construed to cover any other fluid, whether liquid or gas.

BRIEF DESCRIPTION OF DRAWINGS

FIG. 1 is a diagram of a shower that includes a water flow device.

FIG. 2 is a block diagram illustrating components of an example water flow device.

FIGS. 2A-C illustrate example data that may be provided on a display of a water flow device.

DETAILED DESCRIPTION

Figure 3:
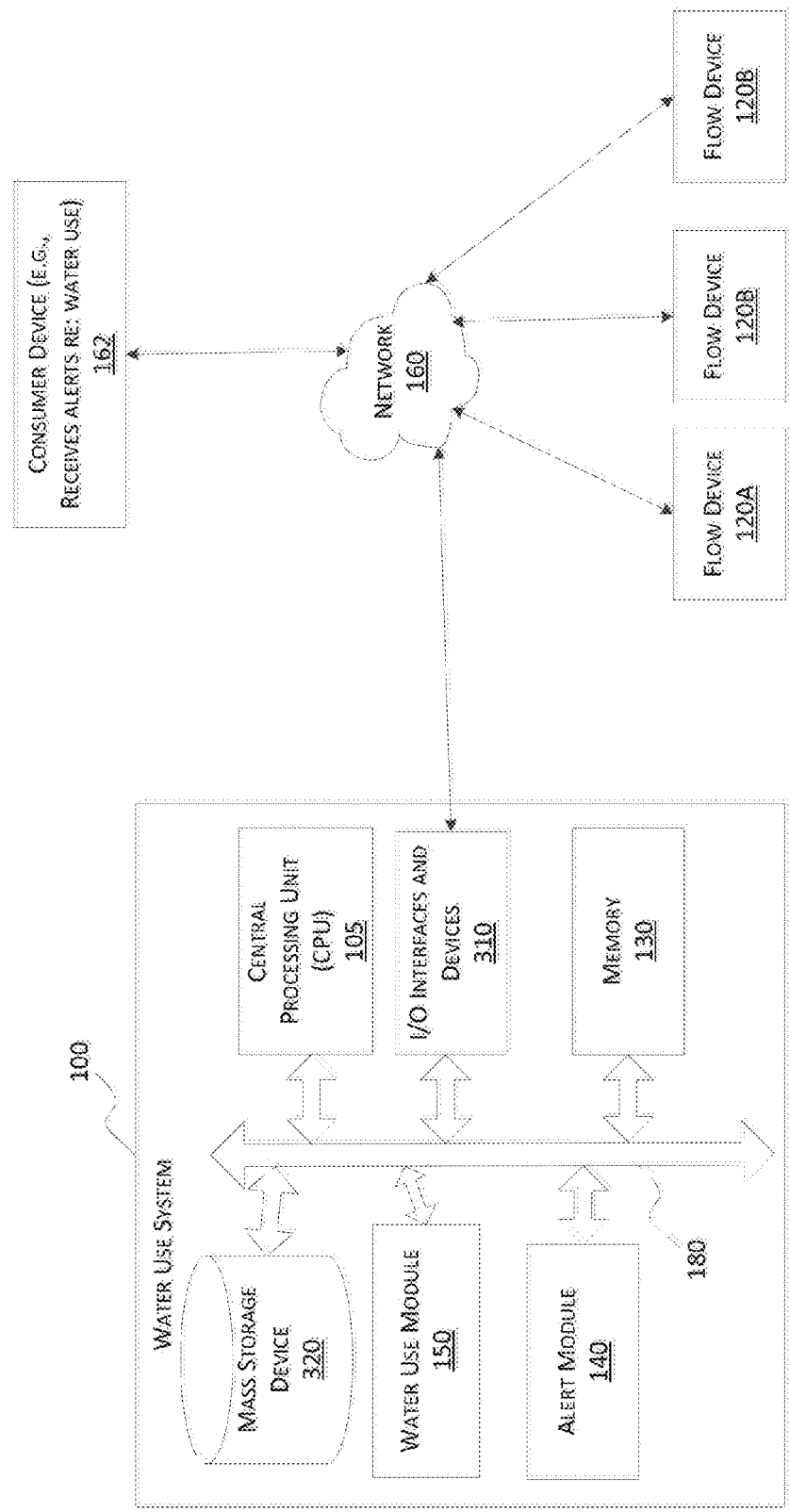
FIG. 3 illustrates a water use system in communication with multiple water flow devices and also in communication with a consumer device.

Although several embodiments, examples and illustrations are disclosed below, it will be understood by those of ordinary skill in the art that the subject matter described herein extends beyond the specifically disclosed embodiments, examples and illustrations and includes additional uses, obvious modifications and equivalents thereof. Embodiments of the invention are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments. In addition, some embodiments include several novel features and no single feature is solely responsible for contributing to the desirable attributes of the embodiments or is essential.

Example Configuration

FIG. 1 is a diagram of a shower 110 that includes a water flow device 120. As shown, the shower 110 includes a shower head 112 that expels water into a water flow 114 when water flow to the shower head 112 is activated. Advantageously, the water flow device 120 is mounted on a wall opposite the shower head 112, such as by being attached to a wall of the shower 110 using suction cups, adhesive patch or other attachment mechanisms. The water flow device 120 may be battery operated (e.g., disposable or rechargeable batteries), so that the water flow device 120 is unobtrusive to the user. In other embodiments, the water flow device 120 may be powered by a conventional wall electrical outlet (e.g., the device may be hard wired or plugged into the electrical grid) located near the shower 110 or by a wireless powering device. This wireless powering device may include two components: a power-sending unit that is connected to an existing wall electrical outlet and transmits an electromagnetic signal and/or a component integrated with the water flow device that is able to receive the electromagnetic energy being produced by the first, power-sending unit. This power it receives can be used to power the water flow device. In other embodiments, the water flow device 120 may be mounted at other positions within the shower 110, or possibly just outside the shower 110. For example, the water flow device 120 may be attached (or otherwise supported or mounted) to the front of the shower (e.g., the side with the showerhead 112), the sides of the shower 110, the ceiling, or the floor of the shower. Additionally, the water flow device 120 is configured to operate in other embodiments where water flow monitoring is desired, such as sinks, hoses, etc. In such embodiments, the water flow device 120 may be mounted in any suitable manner, or may simply be supported on a surface such as a floor or a countertop.

FIG. 2 is a block diagram illustrating components of an example water flow device 120. Depending on the embodiment, water flow devices may include additional or fewer components than are illustrated in FIG. 2, as well as the other figures.

In the embodiment of FIG. 2, the water flow device 120 includes a microprocessor that interfaces with various other components, such as a water flow sensor 122, I/O Devices 123, a power source 124, and a communication circuit 126. The microprocessor 121 may include any suitable circuitry, such as one or more general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration.

In one embodiment, the microprocessor 121 is programmed with logic that allows the microprocessor 121 to determine when water is flowing in the shower 110 and when water ceases to flow in the shower 110, without any input from the user. Example methods of detecting water flow are described further below.

The water flow sensor 122 is configured to detect one or more of an acoustic signal or vibration emitted by the shower head from vibrating, water as it travels through the pipe, water as it exits the pipe as it falls through the air, and/or water as it impacts an object throughout its path either inside or outside the pipe (including the user in the shower or the shower floor or wall of the shower). In one embodiment, the water flow sensor 122 is in communication with the microprocessor 121 in order to provide the acoustic signature of sounds within the shower 110 to the microprocessor 121 for analysis (e.g., in order to determine if water has started or stopped flowing). The water flow sensor 122 may include an acoustic microphone or any other type of acoustic transducer.

In one embodiment, a circuit board of the water flow device 120 includes one or more operational amplifiers and associated components connected to the water flow sensor 122 to provide a low power sensing capability. This circuit may also include a frequency filter tuned to the event being sensed, e.g., the beginning of water flow, within the shower 110. In one embodiment, once the circuit detects water flow, the operational amplifiers turn on a MOSFET device (or other device) that powers the microprocessor 121, I/O devices 123 and/or other associated circuits.

The I/O devices 123 may include any type of display, such as a touch screen display that allows the user to interact with the water flow device by touching the display surface. Additionally, the I/O devices 123 may include one or more speakers or other audible feedback components. The display and speakers may be configured to provide audible and/or visual indications of when the water flow device 120 begins and ends recording water flow use. Examples of information that may be displayed are provided in the discussion below. For example, FIGS. 2A-C illustrate example data that may be provided on a display of the flow sensor 120. In particular, FIG. 2A illustrates that water flow data 131, cost data 132, music/movie output data 133, messaging data 134, and/or communications data 135 may be provided via one or more I/O devices 123. Depending on the embodiment, additional or less data may be provided. FIG. 2B illustrates information on an example water flow sensor 120. In this embodiment, the water flow sensor 120 displays a time for which water flow has been detected, a current flow rate (e.g., based on characteristics of the water pressure, showerhead configuration, acoustic signature of the flowing water, a previously measured flow rate, and/or any other characteristic), and a cost of the shower. In one embodiment, the data shown in FIG. 2B is updated in real time as the user continues to use the shower. Thus, in one embodiment the time increases every second (or other time increment) to show an updated time that the water has been flowing, the quantity of water, and/or the cost of the shower. Finally, FIG. 2C illustrates comparison data from a current day, a current week, and a current month. In one embodiment, user interfaces similar to those in FIGS. 2B and 2C may alternatively be displayed on a water flow device 120, such as in response to an oral command from the user and/or selection of a button or menu option on the water flow device 120.

Returning to FIG. 2, the power source 124 may be a battery, an AC power cord, or any other power source. In an advantageous embodiment, the power source 124 is internal to the water flow device 120 so the water flow device 120 may be more easily installed and is less invasive to the user.

The water flow device 120 includes a housing 125 which, in an advantageous embodiment, is water and moisture resistant. Since the water flow device 120 operates in a shower, the housing 125 may be configured to restrict moisture from entering the water flow device 120 despite high moisture levels and immersion in water through a wide range of temperatures (<0 to >100 degrees Celsius, for example).

In the embodiment of FIG. 2, the water flow device 120 includes a communication circuit 126 that is configured to provide data from the water flow device 122 to one or more external devices and/or to receive data from one or more external devices. In some embodiments, the water flow device 120 does not include a communication circuit 126; that is, the water flow device 120 may not send or receive data to external devices.

In one embodiment, the communication circuit 126 is configured to communicate to a mobile device using the phones own Bluetooth communication capability. In this embodiment, the communication circuit 126 may have the ability to receive the data and then store, process, and/or display the information on the user's mobile device in ways that would provide the user with information regarding the shower. Relevant information could include length of shower, volume of water consumed, time of day shower was taken and data involving past recorded events.

An application on the mobile device (and/or on the water flow device 120) could process the data to observe trends, such as average water consumption during a shower. In other embodiments, the communication circuit 126 may be configured to receive and/or transmit data via any other communication protocols, such as cellular networks or TCP/IP communications via one or more networks (e.g., the Internet). In one embodiment, data provided by the water flow device 120 is transmitted to a central device that may link multiple different devices together (e.g., multiple showers within a house or senior living center or in a Hospitality application, Hotels/Resorts guest room showers) and gather data from all these different devices. This data could be accessed by users to give them information about water usage in their community and elsewhere in the world.

In one embodiment, the water flow device 120 is configured to, upon determining that a shower has ended, execute a program or script or code to establish a connection to an external or peripheral device such as a mobile device (e.g., mobile phone, tablet, smartphone, etc.) or other computer (e.g., personal computer or server). After a connection has been established, data can be transferred to or from the water flow device 120. This data can include data for the shower that just ended, such as length of shower and volume of water used, or it could include images or sound clips that can be processed on board the device and displayed or played to the user.

Below is an outline of example components for a water flow device 120, including certain details regarding an example embodiment of the water flow device 120. As noted above, other water flow devices may include different components and different component settings.
1) A circuit board, with mounted microprocessor, controlling an external display, enclosed in a housing.
2) A water flow sensor capable of detecting a shower in operation. This can be a microphone that has the appropriate sensitivity in the audible and/or ultrasonic frequency range.
3) A display connected to the circuit board and mounted to the housing.
4) A housing, which encases the internal components.
5) An internal energy source, e.g., a 3.7V battery.
6) An attachment/fixture mechanism
7) A wireless communication circuit, e.g., an IC wireless module (WIFI, Zigbee or Bluetooth, etc.), antennae, etc.
8) Firmware to download and upload data to a water flow device (e.g., an app on a mobile device or a central server operated by a provider of the water flow device 120).

In one embodiment, the circuit board [1] is powered by the internal energy source [5] and uses the display [3] to show relevant data of the shower to the user and transmits relevant data to the water use system [7,8]. The housing [4] encases all internal components and contains an opening for the display [3] and the sensing device [2]. The sensing device [2] is connected to the circuit board [1]. The display [3], circuit board [1], sensing device [2] and battery [5] may be packaged and arranged so that the display [3] and sensing device [2] are oriented toward the user. The attachment or fixture [6] may be integrated with the housing to provide a method to secure the device onto either a surface of the shower or on to the shower head piping itself.

Example Communication System

FIG. 3 illustrates a water use system 100 in communication with multiple water flow devices 120 (including water flow devices 120A, 120B, 120C) and also in communication with a consumer device 162. In the embodiment of FIG. 3, the water flow devices 120 detect flow of water in their respective environments (e.g., in different showers of a retirement community or in a Hospitality application, individual home shower, apartment complexes, hospitality facilities, retirement-nursing facilities and complexes, industrial applications, commercial-retail, etc) and provide data to the water use system 100 via any available communication means. Thus, the water flow devices discuss herein may be used in any conceivable environment where fluid flow monitoring is desired.

The water use system 100 may be a system that is operated by an individual that installed and/or operates one or more of the water flow devices 120 (e.g., a manager of the retirement community or hospitality facility) or a provider of the water flow devices 120 (e.g., a central server that receives data from many water flow devices and compiles and organizes the data for display to users, such as via one or more online websites). Thus, in this embodiment the water use system 100 receives data from each of the flow devices 120, such as after the respective flow devices 120 detect that a shower has ended, and compiles the data.

In one embodiment, the water use system 100 provides data from the flow devices 120, such as data on each of the individual devices as well as compiled data for all of the devices (e.g., average water flow) to one or more consumer devices 162. For example, the consumer device 162 may be a mobile phone of a manager of a retirement community.

In the embodiment of FIG. 3, the water use system includes a water use module 150 that is configured to receive data from the various flow devices 120 and calculate water used by each device and an alert module 140 that is configured to monitor water use by the flow devices 120 and to provide alerts to one or more users (e.g., the consumer device 162) in response to an associated condition being met. For example, the alert module 140 may be programmed, such as by the owner of a particular water flow device or an individual responsible for monitoring one or more water flow devices, to include user-defined rules that define what types of alerts should be provided to the consumer device 162. For example, if the flow devices 120 are each positioned in different showers of a retirement community, apartment complex, or hospitality facility, the alert module may include rules that provide alerts (e.g., to a medical alert monitoring service or to the manager of a retirement community, apartment complex, or hospitality facility) if a particular water flow device detects more than a threshold water use and/or time use of a shower (e.g., which could be indicative of an issue with the shower user or shower system). Alternatively, if the flow devices 120 are positioned in a student housing dormitory, the college administrator may set different rules for alerts. In the application of medical alert monitoring, the flow device 120 could alert a Water Use System 100 or other system or service that monitors the health of its users, usually senior citizens, that a shower has been running for a long period of time (e.g., 45 minutes) and may be indicative of the user falling or otherwise incapacitating themselves in or around the shower.

In this embodiment, each of the modules are shown as part of the Water Use System 100. However, in other embodiments, the modules may be distributed across multiple devices, and may be controlled and/or operated by multiple different entities. In other embodiment, the Water Use System 100 may include fewer and/or different modules than are illustrated in FIG. 3.

The term "module," as used herein, refers to any combination of software, firmware, and hardware. For example, certain modules comprise only software code that may be executed by a computer processor, such as the CPU 105. Modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Hardware modules may include connected logic units, such as gates and flip-flops, and/or may be comprised of programmable units, such as programmable gate arrays or processors. Generally, the modules described herein refer to logical modules that may be combined with other modules or divided into sub-modules despite their physical organization or storage.

The network 160 may include any combination of communication networks, such as one or more of the Internet, LANs, WANs, MANs, etc., for example. In the embodiment of FIG. 3, the Water Use System 100 includes a computing system having one or more computing devices (e.g., computers). The computing system may include, for example, a single computing device, a computer server, or a combination of one or more computing devices and/or computer servers. Depending on embodiment, the components illustrated in the Water Use System 100 may be distributed amongst multiple devices, such as via a local area or other network connection. In other embodiments the Water Use System 100 may include fewer and/or additional components that are illustrated in FIG. 3.

The exemplary Water Use System 100 includes one or more central processing units ("CPU") 105, which may each include one or more conventional or proprietary microprocessor(s). The Water Use System 100 may further include one or more memories 130, such as random access memory ("RAM"), for temporary storage of information, a read only memory ("ROM") for permanent storage of information, and/or a mass storage device 320, such as a hard drive, diskette, or optical media storage device. The memory 130 may store software code, or instructions, for execution by the processor 105 in order to cause the computing device (e.g., the Water Use System 100) to perform certain operations, such as determining collection actions for respective consumers.

The methods described and claimed herein may be performed by any suitable computing device, such as the Water Use System 100. The methods may be executed on the computing devices in response to execution of software instructions or other executable code read from a tangible computer readable medium. A computer readable medium is a data storage device that can store data, which can thereafter be read by a computer system. Examples of a computer readable media include read-only memory, random-access memory, CD-ROMs, magnetic tape, flash drives, and optical data storage devices.

The Water Use System 100 is generally controlled and coordinated by operating system software, such as Windows 95, Windows 98, Windows NT, Windows 2000, Windows XP, Windows Vista, Windows 7, Windows 8, Windows Server, Windows Mobile, Unix, Linux (including any of the various variants thereof), SunOS, Solaris, mobile phone operating systems, or other operating systems. In Macintosh systems, the operating system may be any available operating system, such as MAC OS X or iPhone/iPad iOS. In other embodiments, the Water Use System 100 may be controlled by a proprietary operating system. Conventional operating systems control and schedule computer processes for execution, perform memory management, provide file system, networking, I/O services, and provide a user interface, such as a graphical user interface ("GUI"), among other things.

The exemplary Water Use System 100 may include one or more input/output (I/O) devices and interfaces 310, such as a keyboard, trackball, mouse, drawing tablet, joystick, game controller, touchscreen (e.g., capacitive or resistive touchscreen) touchpad, accelerometer, and/or printer, for example. The computing device may also include one or more multimedia devices, such as a display device (also referred to herein as a display screen), which may also be one of the I/O devices 310 in the case of a touchscreen, for example. Display devices may include LCD, OLED, or other thin screen display surfaces, a monitor, television, projector, or any other device that visually depicts user interfaces and data to viewers. The Water Use System 100 may also include one or more multimedia devices, such as speakers, video cards, graphics accelerators, and/or microphones, for example.

In the embodiment of FIG. 3, the I/O devices and interfaces 310 provide a communication interface to various external devices via the network 160. For example, the Water Use System 100 may be electronically coupled to the network 160 via a wired, wireless, or combination of wired and wireless, communication link(s). The network 160 may allow communication with various other computing devices and/or other electronic devices via wired or wireless communication links.

The water flow devices 120, as well as the consumer devices 162, may include any combination of the components discussed above with reference to the Water Use System 100.

Figure 4:
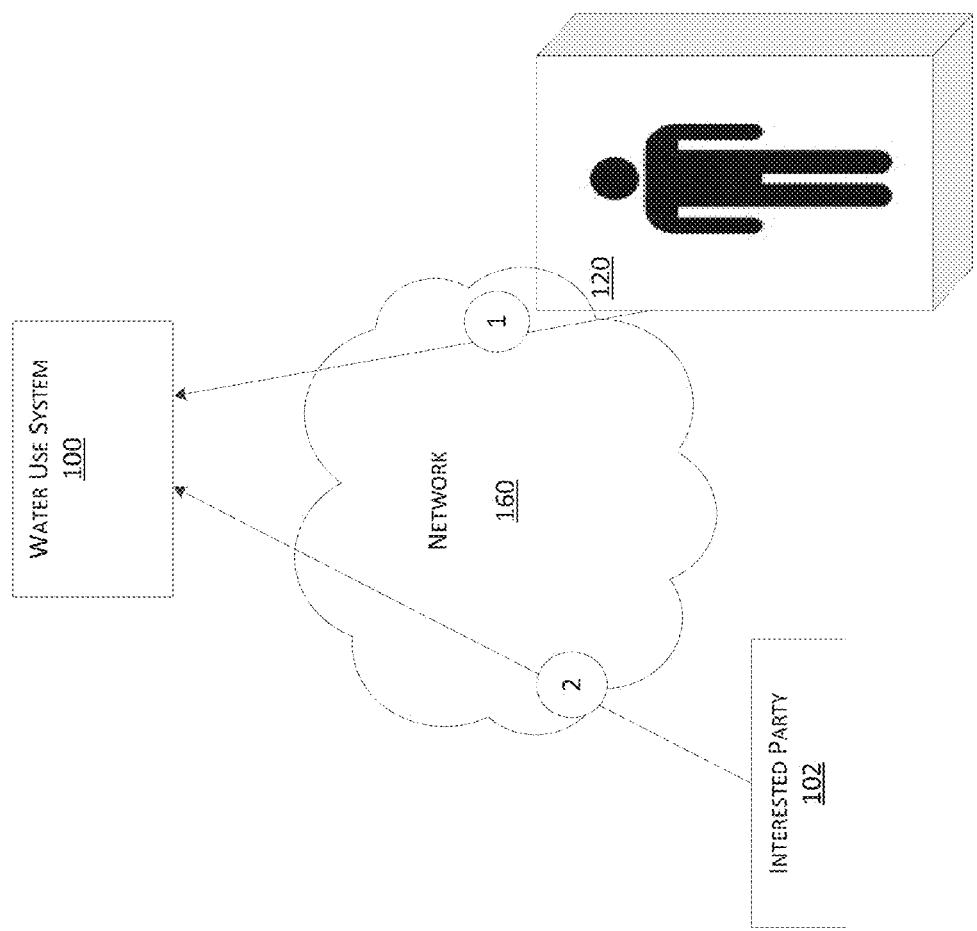
FIG. 4 is a sample data flow diagram, which illustrates a water flow device providing water use data to a water use system via the network.

FIG. 4 is a sample data flow diagram, which illustrates a water flow device 120 providing water use data to a water use system 100 via the network 160. The water use system 100 may then analyze the data (and possibly combine the data with data from other water use devices) and provide information/alerts to one or more interested party 102. In some embodiments, the water flow device 120 may also receive information from the water use system 100 and/or content providers that may provide information for display on the water flow device 120. For example, content providers may include music or movie providers that format music and movies for display on the water flow device 120.

Example Methods of Operation

Figure 5:
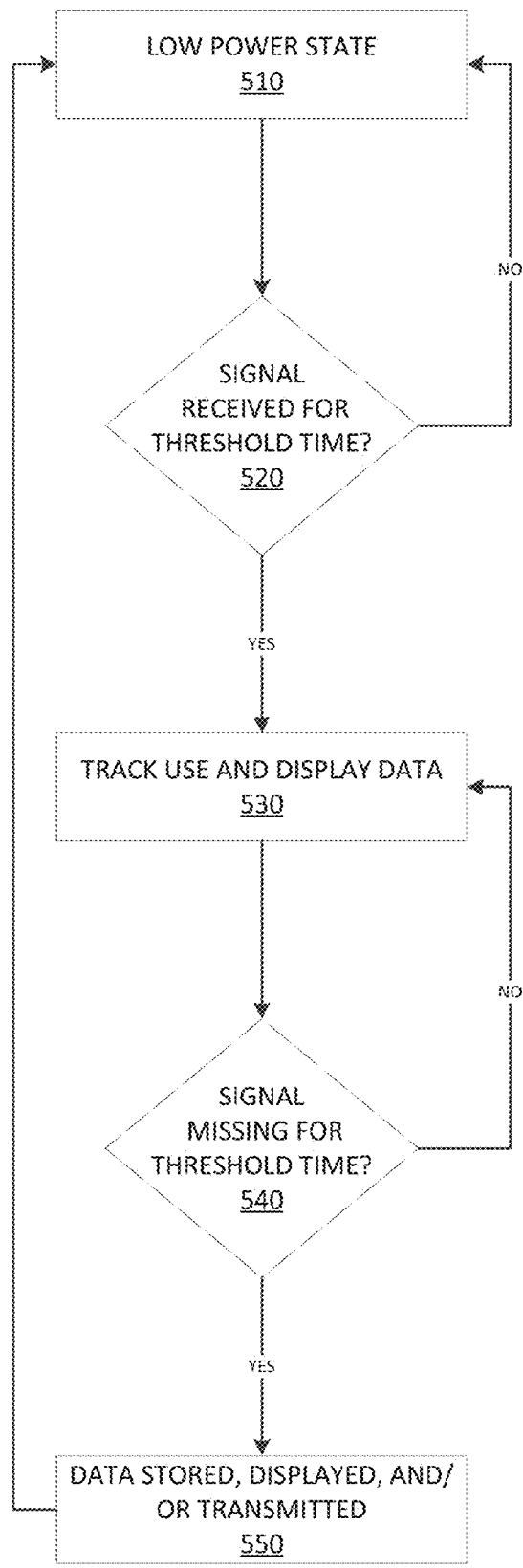
FIG. 5 is a flowchart illustrating one embodiment of a method of determining when water flow has begun and ended, such that the water flow device can track characteristics of a shower (or other water use event).

FIG. 5 is a flowchart illustrating one embodiment of a method of determining when water flow has begun and ended, such that the water flow device 120 can track characteristics of a shower (or other water use event). Depending on the embodiment, the method of FIG. 5 may include fewer or additional blocks and/or the blocks may be performed in a different order than is illustrated. Software code configured for execution on a computing device in order to perform the method of FIG. 5 may be provided on a computer readable medium, such as a compact disc, digital video disc, flash drive, hard drive, memory device or any other tangible medium. Such software code may be stored, partially or fully, on a memory of a computing device, such as the water flow device 120, the water use system 100, and/or other suitable computing devices, in order to perform the method outlined in FIG. 5 by those respective devices. For ease of explanation, the method will be described herein as performed by the water flow device, which should be interpreted to include any one or more of the computing devices noted above and/or any other suitable computing device.

Beginning in block 510, the device maintains a low power state wherein many of the components are powered down while the device is waiting for water flow to monitor. For example, the microprocessor and display may be powered off or placed in a low power state.

In block 520, the device monitors whether a signal from the water flow sensor has been transmitted for a threshold time period, which is indicative of water flow. In one embodiment, an output signal generated by the water flow sensor acts as a switch to control provision of power to the microprocessor. Thus, this output signal is only output when the acoustic signal truly reflects flow of water, rather than simply an arbitrary acoustic waveform. In one embodiment, an electronic filter (or the water flow sensor itself) may include signal processing modules that allow it to screen for what is deemed a true acoustic signal originating from the shower (e.g., water flowing from a showerhead). This signal processing can come in various forms, such as a band-pass filter or high-pass filter, designed to only allow the signals with frequency content above the lower end of the filter and below the upper end of the filter by attenuating frequency components of signals outside of this range. The signal processing can also include any combination of high-pass, low-pass or pass band filters or other signal recognition techniques. Additionally, the thresholds, limits or parameters of these filtering may vary based various attributes, such as the particular monitoring environment, the fluid being monitored, user preferences, etc.

Once a signal is output by the water flow sensor, the microprocessor is powered on and begins to test if the signal is a valid signal originating from the shower water flow rather than from transient noise or other sources of sound in the environment where this water flow device is located. In one embodiment, the microprocessor does this by confirming receipt of the signal for a threshold time period, such as three seconds, in order to confirm that the signal is constant and not a transient event. In one embodiment, the microprocessor and or water flow sensor monitor the amplitude of the signal also in order to determine if the signal truly indicates water flow and/or to perform curve fitting and/or execute other pattern recognition algorithms to determine if the acoustic signature matches that of water (or other fluid being monitored).

In some embodiments, signal recognition techniques may be periodically adjusted, or dynamic, in order to achieve better sensitivity or specificity or both to the type of acoustic signature it is screening for. The signal processing of the device may also receive input from the environment such as though user defined parameters delivered by user controls on the water flow device 120 or on another device where instructions are sent wirelessly or via cable connection to the water flow device 120. The acoustic signature of the water flow has a distinct shape or form in the frequency domain and the pattern of its frequency spectrum (magnitude and phase) is unique and some of the methods to screen for only this signature in the frequency domain have been discussed above.

Screening for the acoustic signature can be done in several ways, some of the analog implementations have been described. Another method to screen for the real acoustic signature of water flow is to monitor its characteristics over a threshold period of time such as 3 seconds. During this time, if the frequency spectrum of the acoustic signal varies in certain ways such as a change in frequency distribution or frequency shift during the course of this threshold time period then the acoustic signature can be determined to be false or transient. This may be done in analog, with an ASIC, DSP, microprocessor, or other logic chip. The system may also be specifically designed to screen for certain transient patterns in the water flow such as pulsating flow, irregular flow, increasing flow rate, etc.

Once a signal is output by the water flow sensor, the microprocessor is powered on and/or enabled and begins to test if the signal is a valid signal originating from the shower water flow rather than from transient noise or other sources of sound in the environment where this water flow device is located. In one embodiment, the microprocessor does this by confirming receipt of the signal for a threshold time period, such as three seconds, in order to confirm that the signal is constant and not a transient event. In one embodiment, the microprocessor and or water flow sensor monitors the amplitude of the signal also in order to determine if the signal indicates water flow.

If the signal does not persist for the threshold time, the method returns to block 510 wherein the water flow device returns to its low power state, e.g., including the microprocessor shutting itself off. If, however, the signal does persists for the requisite amount of time and/or is recognized, the method continues to block 530 where the water flow device begins powering the display and displaying data relevant to the shower. This data can include various data (as explained above), such as the time since the shower started, gallons of water used, time of day, informational data, entertainment data, and/or other desired data.

In block 540, the microprocessor monitors receipt of the signal from the water flow sensor. When the microprocessor first detects that the signal is not received, the microprocessor starts a timer to measure the time period for which the signal has ceased. If the absence of a constant signal lasts for a threshold amount of time, such as one second (or any other predetermined time period), for example, then the microprocessor can determine that the water has stopped flowing from the showerhead, effectively ending the shower. While the absence of a constant signal for a threshold period of time may indicate the water has stopped flowing, a distinct change in the signal such as the magnitude of the signal dropping by a certain amount or the frequency distribution of the signal changing may also signal that the water has stopped flowing, then the microprocessor can determine that the water has stopped flowing from the showerhead, effectively ending the shower. If the signal has not been received for the threshold time, the method continues to block 550 where the data is stored, displayed, and/or transmitted. In one embodiment, the water flow device includes a storage medium, such as a flash memory device, that stores water flow data internally that can be recalled and viewed by the user later. In some embodiments, the data is transmitted to another device, such as a device of the user and/or a central server, such as the water use device 100 discussed above. In one embodiment, at block 550 the device displays data relevant to the shower, such as the time in the shower and volume of water used, for the user to observe for a certain period of time, such as 10 seconds, for example. After storing, displaying, and/or transmitting data, the method returns to block 510 where the device returns to the low power state so that battery life may be prolonged. Depending on the embodiment, the battery may be disposable (e.g., one time use) or rechargeable (e.g., capable of being recharged by plugging into an electrical outlet).

Returning to block 540, if the time that the shower signal fails to be received does not last at least the threshold time, then the method returns to block 530 where the device continues to track use and display data.

Figure 6:
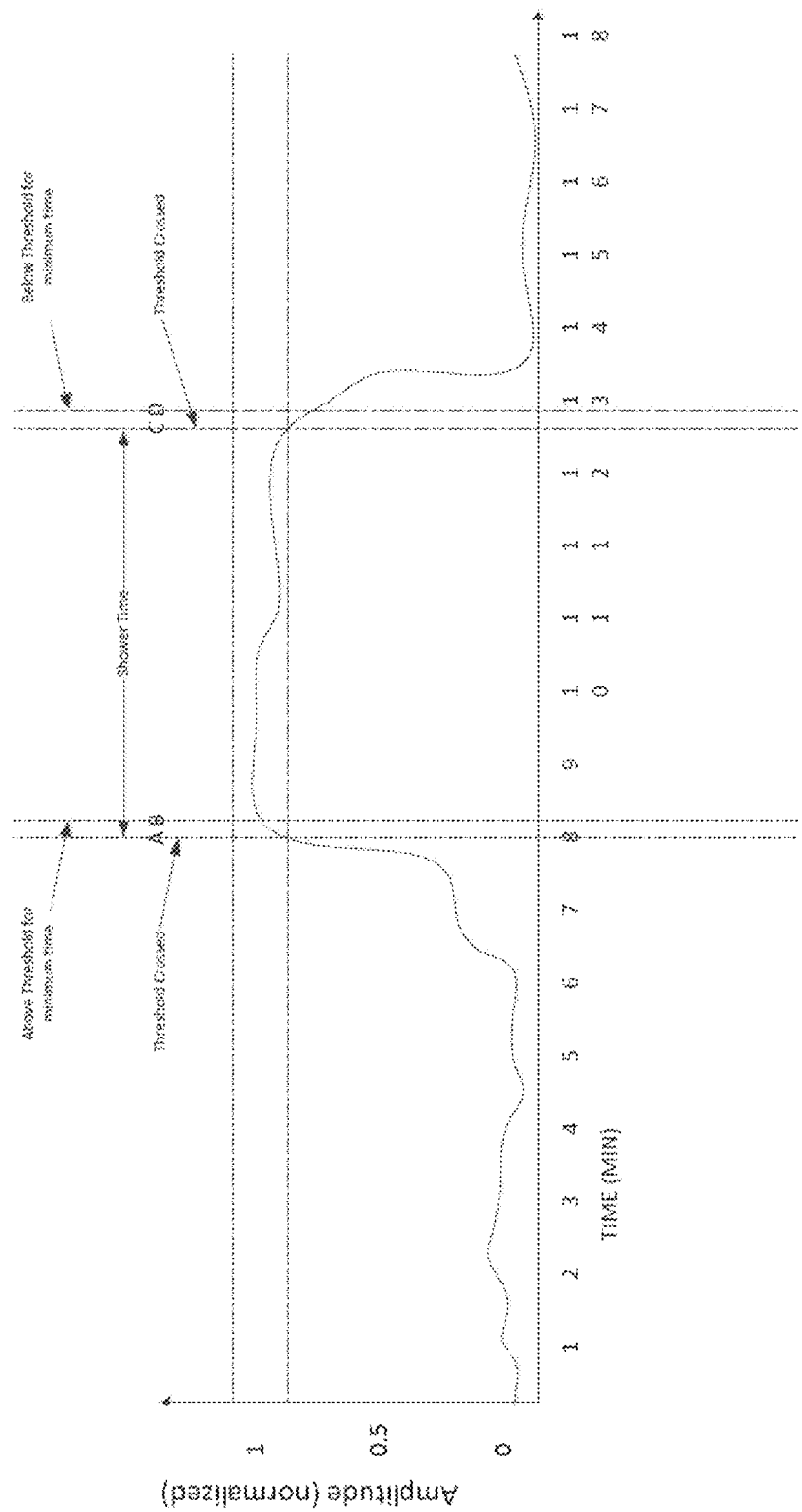
FIG. 6 is a graph showing the averaged amplitude of the signal within a particular frequency band of interest (e.g., 20 kHz-25 kHz) over time.

The spectral distribution of the signal may be unique to water flowing in a shower and it is this signature along with the amplitude of the signal that is used to differentiate the case where water is indeed flowing in a shower (or any other fixture, plumbing, faucet, sink, pipe, valve, etc.). FIG. 6 is a representative graph showing the averaged amplitude of the signal within a particular frequency band of interest (e.g., 20 kHz-25 kHz) over time. The dependent variable is normalized amplitude to represent threshold amplitudes that can be set, which will determine when the signal is ON or OFF.

In the example of FIG. 6, when the normalized amplitude enters the threshold level at time A (e.g., about the 8 min. mark of the graph), the water flow sensor begins to transmit an output signal causing the microprocessor to be powered on (or move from a low power state to a higher power state). The microprocessor may then monitor the length of time that the signal is received, and possibly other characteristics of the signal, in order to determine if water flow should be monitored. As discussed above, in one embodiment the microprocessor is configured to begin recording water flow data in response to detecting the signal for a threshold time. In the embodiment of FIG. 6, a threshold time has been met at time B (e.g., where B-A is the determined threshold time, such as 1 sec., 2 sec., 3 sec., etc.). Thus, at time B, the microprocessor records the beginning of a shower (or other water flow event). The microprocessor continues to monitor for receipt of the signal and, when the signal is no longer received at time C, the microprocessor begins a timer to determine if the signal will not be received for the threshold time period. In the example of FIG. 6, the threshold time period is met at time D, which is when the microprocessor determines that the shower has ended. The microprocessor in the water flow device may monitor other aspects of the received signal after time C to determine if the shower has ended (e.g., at time C). These aspects may include fluctuations or changes in signal amplitude or frequency spectrum distribution that are greater than a predetermined allowable limit. Alternatives to a microprocessor such as ASIC, FPGA or other circuit design, either analog or digital, may be used to achieve the monitoring of the flow event and determining whether flow is occurring or not. As discussed above, the microprocessor may then store, transmit, and/or display various data regarding the latest shower. The length of the shower may be determined in multiple ways, such as by calculating the time period associated with C-A or D-B.

In other embodiments, the water flow sensor may continuously send a signal to the microprocessor, which may be in a low-power state at block 510 (FIG. 5). In this embodiment, the microprocessor may monitor the frequency and/or amplitude of the received signal to determine when the microprocessor should be turned to full power and begin recording data regarding a shower. In other embodiments, the circuitry for detecting the beginning and end of a shower may be provided in other manners.

In other embodiments, the frequency range that is monitored by the water flow device may be different. For instance, narrower bands (e.g., 23-25 kHz), broader bands (e.g., 18-27 kHz) or a combination of more than one band of different frequency and bandwidth may be used to screen for unique patterns in the signal.). For example, if water flow in a pipe is monitored, the monitoring frequency may have a wider spectrum. Depending on the embodiment, the monitored spectrum may be configured to detect water moving in a pipe, water exiting the showerhead, moving through the air, and/or hitting a user and/or shower surface.

Figure 7:
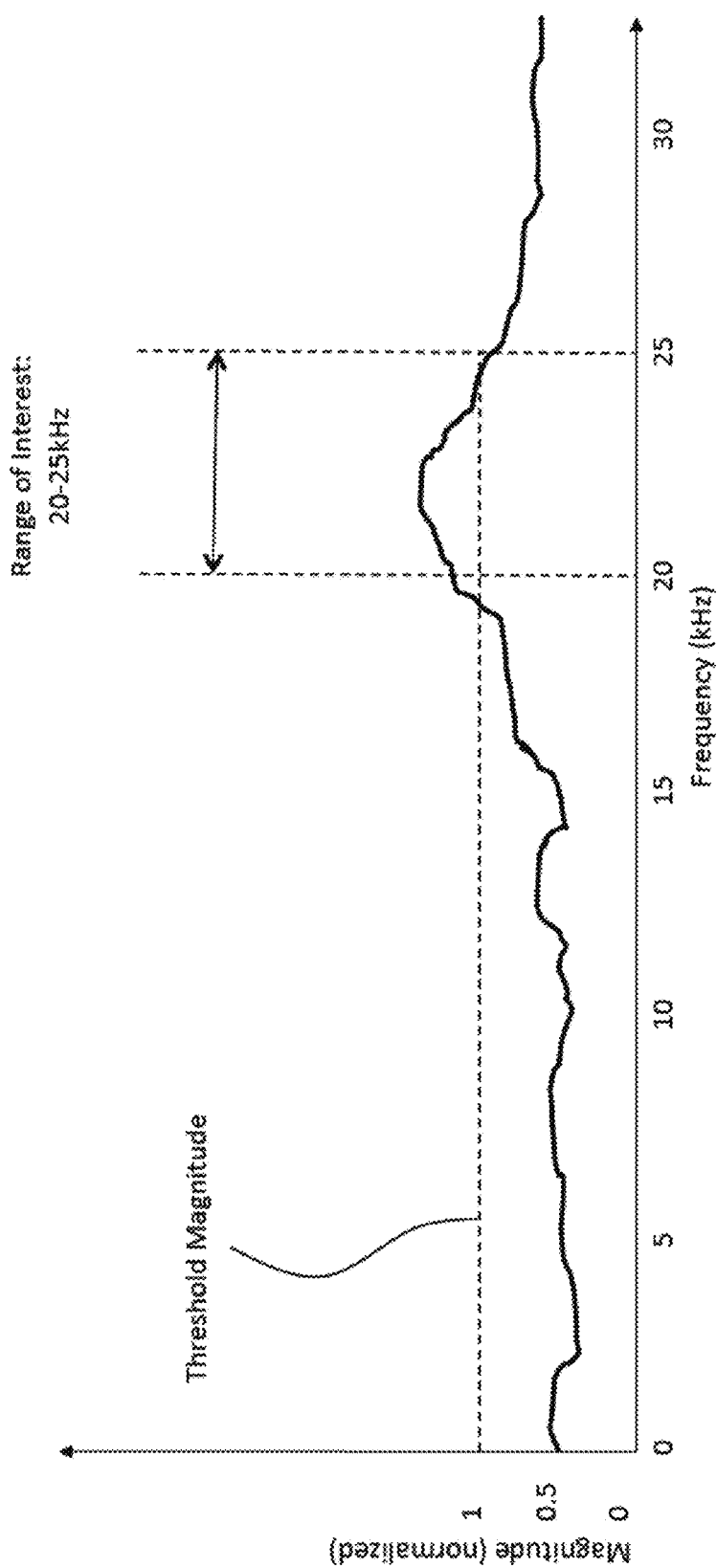
FIG. 7 is a graph that shows a sample acoustic signature of a running shower.

FIG. 7 is a graph that shows a sample acoustic signature of a running shower. This acoustic signature is presented as a normalized magnitude plot in the frequency spectrum from 0 Hz to 30 kHz. The magnitude is normalized because the sensitivity of the water flow device can be adjusted and the absolute threshold can be variable. In this embodiment, the water flow device 120 will screen for only the frequencies between 20 kHz and 25 kHz. Only signals with magnitude above a predetermined threshold value within this frequency band will indicate that water is flowing and this screening can form the basis of the logic of the water flow device 120 described above.

The example methods discussed above are only examples of methods for detecting a shower starting, stopping or pausing. Electronics involved can be implemented in various ways that could achieve similar functions. For example, instead of performing any analog signal processing the device could perform all signal processing and calculations using software; a microprocessor could receive data via an analog-to-digital converter and then perform any signal processing or other mathematical functions to try and detect a true "shower" signal. Likewise, instead of using a microprocessor to gauge if a signal has been above a threshold for a predetermined period of time, the device could perform all signal processing in analog along with ASIC and/or FPGA chips. The graphic display is also only one implementation of a user interface. Any combination of audio, visual and even tactile interfaces could provide similar functionality to the user. In one embodiment other sensors besides (or in addition to) an acoustic sensor may be used to detect water flow, such as a vibration sensor, a temperature sensor like thermocouples and thermistors, an optical sensor such as infrared cameras, and/or a humidity sensor to detect water flow in a shower, bathtub, basin, and/or any other location where water can be configured to flow.

Other Features

In some embodiments, the water flow device may receive a signal and/or data sent to the device (e.g., via WiFi) that includes advertisement information (e.g., information usable to display and/or audibly play an advertisement on the flow device). For example, the flow device may be configured to play a pre and/or post shower advertisement related to a consumer product. In one embodiment, the advertisement is selected based on profile and/or other data of the consumer, such as via information accessible in a social media account of the consumer. In one embodiment, the individual watching the advertisement may interact with the advertisement, such as via a touchscreen interface or voice commands, such as by, for example, pressing a Yes or No box on the screen if they want a sample of the product sent to them to try out.

In some embodiments, the water flow device is configured to receive information regarding certain attributes of a mobile device (e.g., cellphone, smartphone, audio device, or tablet computer) that is in communication with the water flow device via a Bluetooth (or other near field) communication channel (or via a WiFi connection to a remotely located mobile device). For example, the water flow device may be configured to provide visual and/or audible notice of receipt of a voice call, voicemail, text message, push notification, update from an app, and/or any other activity associated with the mobile device. For example, in one embodiment the water flow device may be configured to provide a particular audible alert when a phone call is received on the user's cell phone, and may further be configured to provide another alert when a voicemail message is left on the user's cell phone. Similarly, the water flow device may be configured in one embodiment to display the actual text of a message received on a cell phone (e.g., on a water resistant display screen) or audibly speak the text of such a message (e.g., text to speech).

In some embodiments, the water flow device may be configured to display information to the user, such as may be pre-stored on the device and/or may be obtained from another source, such as via a network connection (e.g., WiFi) or near field communication with a mobile device. In one embodiment, the water flow device is configured to display trivial pursuit type questions/facts related to water (and/or any other topic), such as when flowing water is first detected and/or at various intervals afterwards. In one embodiment, the user can configure a frequency and/or type of information displayed. In one embodiment, the user provides responses to such trivia questions via a touchscreen interface and/or voice commands.

SUMMARY

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

All of the methods and processes described above may be embodied in, and partially or fully automated via, software code modules executed by one or more general purpose computers. For example, the methods described herein may be performed by the water flow device 120, the water use device 100, and/or any other suitable computing device. The methods may be executed on the computing devices in response to execution of software instructions or other executable code read from a tangible computer readable medium. A tangible computer readable medium is a data storage device that can store data that is readable by a computer system. Examples of computer readable mediums include read-only memory, random-access memory, other volatile or non-volatile memory devices, CD-ROMs, magnetic tape, flash drives, and optical data storage devices.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A device for monitoring use of a shower, the device comprising:
   a mounting mechanism for mounting the device on a surface of the shower so that the device is not in direct contact with water carrying components of the shower;
   an acoustic transducer;
   a processor configured to:
   maintain the device in a first operational mode wherein the processor:
      receives acoustic data from the acoustic transducer;
      determines an amplitude and/or signal pattern of the acoustic data within a predetermined frequency range, wherein the predetermined frequency range includes a peak frequency of sound created by water exiting a shower head or water flowing;
      in response to determining that the amplitude and/or signal pattern is above a predetermined threshold for a first predetermined time period, initiating a second operational mode of the device, wherein in the second operational mode, the processor:
         tracks a time period for the device in the second operational mode;
         monitors the amplitude and/or signal pattern of the acoustic data within the predetermined frequency range;
         in response to determining that the amplitude and/or signal pattern of the acoustic data is below the predetermined threshold for a second predetermined time period, transmitting the tracked time period to an external device and initiating return of the device to the first operational mode.

2. The device of claim 1, wherein the acoustic transducer comprises a microphone.

3. The device of claim 1, wherein the predetermined frequency range comprises frequencies between about 20 kHz to 25 kHz.

4. The device of claim 3, wherein the predetermined frequency range comprises frequencies between about 23 kHz to 25 kHz.

5. The device of claim 1, wherein the predetermined threshold is an amplitude of more than about 50% higher than an amplitude of the acoustic data within the predetermined frequency range when water is not exiting the shower head.

6. The device of claim 1, wherein the predetermined threshold is an amplitude of more than about twice an amplitude of the acoustic data within the predetermined frequency range when water is not exiting the shower head.

7. The device of claim 1, wherein the first predetermined time period is about 500 milliseconds and the second predetermined time period is about 750 milliseconds.

8. The device of claim 1, wherein the device consumes less power in the first operational mode than in the second operational mode.

9. The device of claim 1, wherein the processor is further configured to receive data from a mobile computing device and to provide a visible and/or audible indication of the received data.

10. The device of claim 9, wherein the mobile computing device comprises a cellular phone and the visible and/or audible indication indicates that a phone call and/or text message has been received on the cellular phone.

11. The device of claim 10, wherein the device comprises a text to voice module configures to convert textual data in the received data into audible words that are played on one or more speakers of the device.

12. The device of claim 9, wherein the mobile computing device communicates with the device via a Bluetooth communication link.

13. The device of claim 1, wherein the tracked time period is transmitted via one or more networks to the external device.

14. The device of claim 13, wherein the tracked time period is accessible by other computing devices also in communication with the external device via one or more networks.

15. The device of claim 13, wherein the external device comprises an online portal that stores the tracked time period and provides summary information regarding multiple tracked time periods from the device.

16. The device of claim 1, wherein the processor is further configured to receive advertising data from the external device or another device.

17. The device of claim 1, wherein the processor is further configured to receive water trivia data from the external device or another device.

18. The device of claim 1, wherein the device comprises a touch sensitive screen that is configured to receive feedback from the user.

19. The device of claim 1, wherein the mounting mechanism comprises one or more suction cups and is configured for mounting in a shower.

20. The device of claim 1, wherein device further comprises a battery compartment configured to receive one or more batteries configured for powering the processor.

21. A device for monitoring use of a shower, the device configured for placement outside of direct contact with water carrying components of the shower, the device comprising:
  an acoustic transducer; and
  a processor configured to:
    maintain the device in a first operational mode wherein the processor:
      receives acoustic data from the acoustic transducer;
      determines an amplitude and/or signal pattern of the acoustic data within a predetermined frequency range, wherein the predetermined frequency range includes a peak frequency of sound created by water exiting a shower head or water flowing;
      in response to determining that the amplitude and/or signal pattern is above a predetermined threshold for a first predetermined time period, initiating a second operational mode of the device, wherein in the second operational mode, the processor:
        tracks a time period for the device in the second operational mode;
        monitors the amplitude and/or signal pattern of the acoustic data within the predetermined frequency range;
        in response to determining that the amplitude and/or signal pattern of the acoustic data is below the predetermined threshold for a second predetermined time period, transmitting the tracked time period to an external device and
        initiating return of the device to the first operational mode.

22. A non-transitory computer readable storage device storing a water use module comprising software instructions executable by a computing device placed outside of direct contact of water carrying components, the computing device having an acoustic transducer and a processor, execution of the water use module causing the computing device to:
  maintain the water use module in a first operational mode wherein the processor:
    receives acoustic data from the acoustic transducer;
    determines an amplitude and/or signal pattern of the acoustic data within a predetermined frequency range, wherein the predetermined frequency range includes a peak frequency of sound created by water exiting a shower head or water flowing;
    in response to determining that the amplitude and/or signal pattern is above a predetermined threshold for a first predetermined time period, initiating a second operational mode of the water use module, wherein in the second operational mode the processor:
      tracks a time period for the water use module in the second operational mode;
      monitors the amplitude and/or signal pattern of the acoustic data within the predetermined frequency range;
      in response to determining that the amplitude and/or signal pattern of the acoustic data is below the predetermined threshold for a second predetermined time period, transmitting an alert indicating the tracked time period to an external device; and
  initiating return of the water use module to the first operational mode.

* * * * *